United States Patent [19]

Walton

[11] 4,307,728

[45] Dec. 29, 1981

[54] PORTABLE DEVICE FOR MEASURING HEARTBEAT RATE WITH COMPENSATION FOR EXTRANEOUS SIGNALS

[76] Inventor: Charles A. Walton, 19115 Overlook Rd., Los Gatos, Calif. 95030

[21] Appl. No.: 108,503

[22] Filed: Dec. 31, 1979

[51] Int. Cl.³ .............................................. A61B 5/02
[52] U.S. Cl. .................................... 128/687; 128/722
[58] Field of Search ............................... 128/687–690, 128/722, 706, 736, 672; 364/417

[56] References Cited

U.S. PATENT DOCUMENTS

| | | | |
|---|---|---|---|
| 3,742,937 | 7/1973 | Manuel et al. | 128/690 |
| 3,802,698 | 4/1974 | Burian et al. | 128/707 |
| 3,872,455 | 3/1975 | Fuller et al. | 340/870.05 |
| 3,880,145 | 4/1975 | Blick | 128/672 |
| 3,986,498 | 10/1976 | Lewis | 128/706 |
| 4,052,979 | 10/1977 | Scherr et al. | 128/690 |
| 4,063,551 | 12/1977 | Sweeney | 128/690 |
| 4,078,551 | 3/1978 | Wohltjen et al. | 128/681 |
| 4,120,296 | 10/1978 | Prinz | 128/690 |
| 4,182,315 | 1/1980 | Vas et al. | 128/687 |
| 4,202,350 | 5/1980 | Walton | 128/690 |

Primary Examiner—Robert W. Michell
Assistant Examiner—Francis J. Jaworski
Attorney, Agent, or Firm—Gerald L. Moore

[57] ABSTRACT

A device mounted on and coupled to the body of the wearer for measuring and visually displaying the pulse rate or other body functions. A primary sensor is positioned on the skin at a position to sense arterial pressure variations and generate a pulse signal responsive thereto while a secondary sensor is positioned close by to generate signals due to extraneous influences of the body and environment. These extraneous signals are subtracted from the pulse signal to increase the accuracy thereof.

2 Claims, 3 Drawing Figures

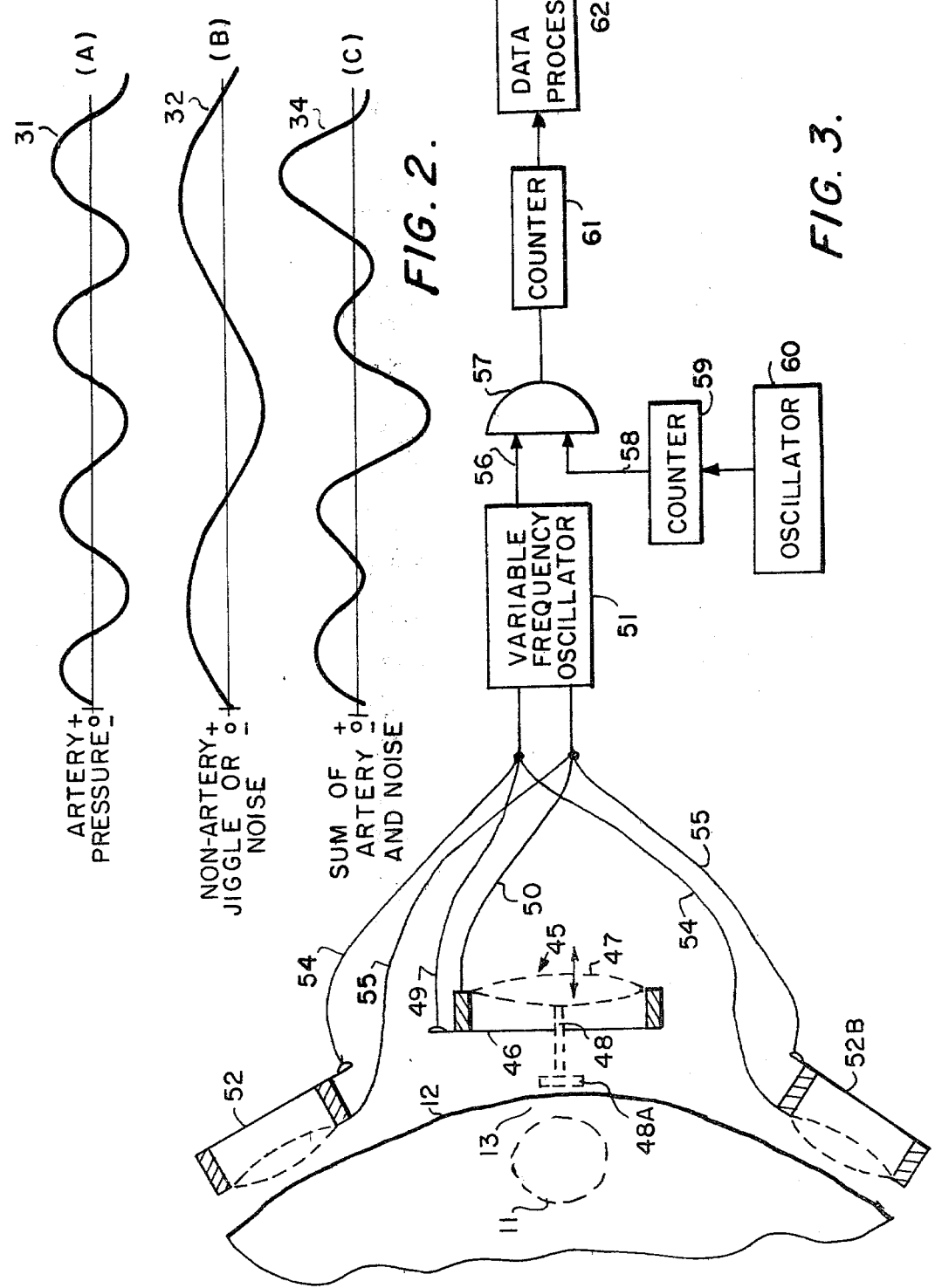

PORTABLE DEVICE FOR MEASURING HEARTBEAT RATE WITH COMPENSATION FOR EXTRANEOUS SIGNALS

RELATED APPLICATIONS

This invention is an improvement on the type of device disclosed in the U.S. application Ser. No. 905,774, entitled: Device for Measuring Pulse, Breathing and Running Rate for Joggers, filed on May 15, 1978, with the same inventer and now U.S. Pat. No. 4,202,350.

BACKGROUND OF THE INVENTION

The present invention is advantageous mainly for individuals performing exercises such as jogging who need to know continuously their pulse rate and other body functions so that they can regulate their rate of exercise. It has been found that sensors which are convenient to mount on the body are also sensitive to extraneous influences not related to the body function being detected. For instance, with a pulse detector such as that described in the above-mentioned application, other influences such as movement of the body, the arm and the wrist can cause pressure changes which make it more difficult to detect the arterially caused pressure changes by sensors positioned on the skin.

In addition other body condition sensors such as for example color measuring devices are known which detect blood flow due to changes in the color of the capillaries. These devices are known to be responsive to other changing body conditions such as movement or pressure on the body in the area of the capillaries being sensed. Other devices sense changes in electrical potentials in the body to indicate body functions. Also skin temperatures are known to indicate body conditions and have been sensed to measure body conditions.

The purpose of the subject invention is to compensate for the effects of other influences on such sensors so that the signal actually generally more clearly reflects the body function being detected.

SUMMARY OF THE INVENTION

A device for measuring pulse rate or like body functions which can be sensed through the skin comprising a first sensor positioned to detect a body condition indicating the body function desired and to generate a first signal responsive thereto, a second sensor positioned so as not to detect the body function desired but positioned in near proximity to the first sensor for generating a second signal responsive to other extraneous conditions in the body which are also detected by the first sensor, and circuit means for subtracting the second signal from the first signal so as to eliminate such extraneous influences and render a compensated signal which is more accurately responsive to the body function being detected.

DESCRIPTION OF THE DRAWINGS

FIG. 2 shows signals representing the pulse being detected; and

FIG. 3 is a second embodiment of the invention.

DESCRIPTION OF THE INVENTION

Figure 1:
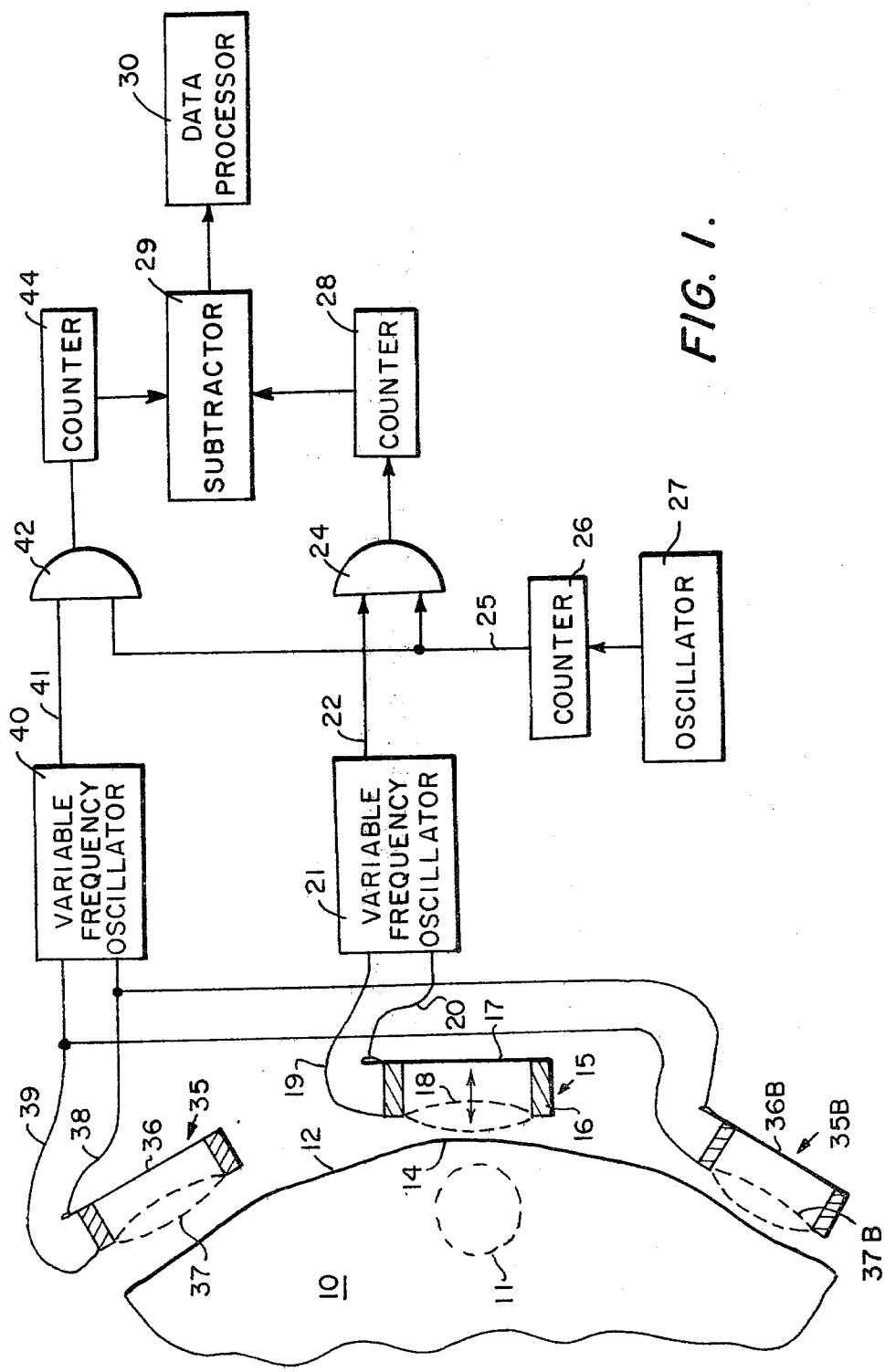
FIG. 1 shows the first embodiment of the invention in a schematic and block diagram form.

The invention is embodied in a device for measuring body functions such as pulse in the manner defined in the previously-identified application, Ser. No. 905,774. It should be understood, however, that the invention will function with equally beneficial results in other devices for detecting body functions such as for example, the color detecting skin temperature and electrical potential measuring devices previously mentioned. Such a device can be fixed to the body of the user preferably for measuring such body functions as pulse rate so that the exercise tempo can be monitored and regulated. Other body functions that can be detected by use of the present invention are those generally indicated by some movement, color or other condition of the skin or of a portion of the body such as the breathing rate or the pace rate. The pulse rate is detected in the example described herein.

As shown in FIG. 1 the wrist 10 of the user includes an artery 11 which, as the blood surges therethrough, produces a movement at the skin surface 12 in the area 14. For detecting the pulse rate there is provided a prmary sensor 15 enclosed in a case 16 and incorporating a fixed plate 17. A plate 18 is positioned adjacent the skin. This plate is moved in a direction towards and away from the first plate as the skin moves with the pulse. By detecting the capacitance change between the plates through the conductors 19 and 20 and supplying this first signal to a variable frequency oscillator 21, there can be generated an output signal having a frequency responsive to and changeable with the pulse rate as detected in the wrist. This output signal is supplied through the conductor 22 to an AND gate 24 along with a signal supplied through the conductor 25 from a counter 26. The counter is supplied with a constant frequency signal from an oscillator 27.

There is supplied to the counter 28 a periodic sampling of the first signal from the variable frequency oscillator 21 which sampling takes place several times for each expected pulse. At a predetermined periodic rate a plurality of frequency signals are supplied through a subtractor 29 to a data processor 30 and by comparing adjacent signals it can be determined whether the frequency is increasing or decreasing. Therefore as described in the previous application, by detecting the change and direction of change of the frequency signals the pulse of the individual can be detected. As shown in FIG. 2 the pulse signal should appear somewhat like the curve 31 which represents arterial pressure along the ordinate and time along the abscissa.

Because the pulse rate is measured by sensing pressure changes of the artery which in turn is detected by movement of the skin, other movements of the skin in the general area in which the sensor is positioned can affect the pulse reading. For instance movement of the whole body as in jogging or movement of the arm and wrist caused by operation of muscles and tendons can cause extraneous or random skin movement which the sensor detects and incorporates in the generation of the first signal. An example of such extraneous influences is shown as the wave form 32 in FIG. 2 which in this instance is primarily due to skin movement resulting from the flexing of muscles and tendons in the wrist. Thus the skin movement influences cause the transducer 15 to generate a signal resulting in the variable frequency oscillator transmitting a frequency signal similar to the wave form 34. The wave form 34 is the sum of wave forms 31 and 32. While this wave form roughly represents the pulse of the user, it is obvious that the signal is much harder to interpret.

In accordance with the present invention there is provided a secondary transducer with a related circuit to cancel most of the extraneous influences from the signal representing the body function desired. Accordingly there is provided one or more secondary sensors 35 and 35B which incorporate a fixed plate 36 and a movable plate 37 functioning in the same manner as the primary sensor 15. The additional sensors are positioned in close proximity to but spaced from the first sensor 15 so as not to detect the arterial pressure-caused skin movement. For instance the sensors are positioned to the side of the primary sensor and therefore to the side or around the wrist so as to be spaced from the artery beneath the skin. The capacitance of the secondary sensor is detected through the conductors 38 and 39 to regulate a variable frequency oscillator 40 which functions in the same manner as the oscillator 21. This oscillator supplies a signal through the conductor 41 to an AND gate 42 receiving at the other terminal the signal from the counter 26 through the conductor 25. From the AND gate there is supplied a signal to the counter 44 which functions in the same manner as the counter 28 to supply a signal to the subtractor 29. The subtractor serves to subtract the second signal supplied by the counter 44 from the primary signal of the counter 28 such that the result is the supplying of a compensated signal more nearly representing the waveform 31. Since the secondary sensor 35 is not subject to the arterial pressure changes there is no deletion of the magnitude of that signal but only a deletion of the extraneous signals which are common to both the primary sensor 15 and any secondary transducers 35. The output of subtractor 29 is used by the data processor 30 for calculation and display.

In FIG. 3 is shown a second embodiment of the invention in which the primary sensor 45 incorporates a fixed plate 46 and a movable plate 47. In this embodiment the plate 45 is mounted on the side of the fixed plate 46 opposite the skin and is actuated by a small rod 48 which extends through a center opening in the plate 46 and contacts a pad 48A on the wrist skin. Thus the capacitance of this sensor decreases as the pressure in the artery 11 increases which normally causes the skin to expand outward and is sensed through the conductors 49 and 50 connecting to a variable frequency oscillator 51. Similarly there are positioned to the side of the primary sensor 45 the secondary sensors 52 and 52B which also supply a signal in the form of a capacitance value to the same variable frequency oscillator through the conductors 54 and 55 parallel connected with the conductors 49 and 50. The output signal from the variable frequency oscillator is fed through the conductor 56 to an AND gate 57 receiving a signal through the conductor 58 from a counter 59 and a crystal oscillator 60. This AND gate signal is fed to a counter 61 which in turn supplies a signal for interpretation to the data processor 62.

Thus the circuit of FIG. 3 functions in the same manner as the circuit of FIG. 1 with the exception that the extraneous signal influences are deleted by subtracting directly the signals resulting from the pressure variations influencing the capacitance of the sensors 45 and 52. For instance the capacitance of the primary sensor 45 decreases as the skin expands outward while the capacitance of the secondary sensors 52 decreases. Thus the capacitance signals are subtractive because of the opposing operations of the transducers and in that manner the extraneous signal influences are deleted. The variable frequency oscillator is selected to be responsive to the change in capacitance of the primary sensor as modified by the compensating signal or capacitance of the secondary sensors.

It can be seen that the present invention provides means for improving the output signal from a body function sensor by compensating for extraneous signal influences. It is also understood that a similar concept can be used in detecting the breathing rate wherein the expansion of the chest is detected. In this instance the chest expansion signal would include other body movement influences which could be detected by another transducer and subtracted from the signal of the primary transducer.

In the instance of photoelectric sensing of skin color changes to detect heartbeat, one or more auxiliary photoelectric sensors whose signals are electrically subtracted from the primary sensor, are used to obtain a signal more representative of the body variable being sensed.

Also as stated before, the invention can be used to cancel out extraneous effects while detecting body functioning in other ways, such as color variations, temperatures and electrical potentials. In each of these systems, extraneous body movements or conditions can be compensated for with multiple sensors.

The invention claimed:
1. A device for measuring a primary body function of the wearer, comprising in combination:
 a primary capacitor adapted for positioning in contact with a first portion of the body for generating a primary signal comprising a capacitive value which changes directly responsive to movement of the body primarily due to the primary body function being detected;
 a secondary capacitor adapted for positioning in contact with a second portion of the body adjacent said first portion for generating a secondary signal comprising a capacitive value which changes indirectly responsive to movement of the body primarily due to body functions other than the primary body function;
 circuit means for parallel connecting said primary and secondary capacitors so the capacitive values are additive to generate a differential capacitive signal;
 a variable frequency oscillator connected to act responsive to the differential capacitive signal to generate a frequency signal having a frequency responsive to the capacitive signal; and
 a counter for generating a digital output signal responsive to the frequency signal indicating the primary body function of the wearer.

2. A device for measuring a primary body function of the wearer, comprising in combination:
 a primary capacitor adapted for positioning in contact with a first portion of the body for generating a primary signal comprising a capacitive value which changes directly responsive to movement of the body primarily due to the primary body function being detected;
 a secondary capacitor adapted for positioning in contact with a second portion of the body adjacent said first portion for generating a secondary signal comprising a capacitive value which changes responsive to movement of the body due to body functions other than the primary body function;

first and second variable frequency oscillators connected to said primary and secondary capacitors respectively for generating first and second frequency signals responsive in frequency to the respective capacitive values of the respective capacitors;

first and second counters connected to receive said first and second frequency signals respectively and generate first and second digital output signals; and means to subtract said first and second digital output signals and generate a differential output signal responsive to said primary body function.

* * * * *